(12) United States Patent
Kwon et al.

(10) Patent No.: US 7,851,605 B2
(45) Date of Patent: Dec. 14, 2010

(54) RECOMBINANT VACCINE FOR PREVENTING AND TREATING PORCINE ATROPHIC RHINITIS

(75) Inventors: Moo Sik Kwon, Gangseo-gu (KR); Woo Seok Shin, Geochang-gun (KR); Bo Ram Han, Bucheon-si (KR)

(73) Assignee: Sungkyunkwan University Foundation for Corporate Collaboration, Gyeonnggi-do (KR)

( * ) Notice: Subject to any disclaimer, the term of this patent is extended or adjusted under 35 U.S.C. 154(b) by 280 days.

(21) Appl. No.: 11/977,327

(22) Filed: Oct. 24, 2007

(65) Prior Publication Data

US 2009/0068217 A1 Mar. 12, 2009

(30) Foreign Application Priority Data

Jan. 31, 2007 (KR) .................. 10-2007-0009776

(51) Int. Cl.
*C07H 21/04* (2006.01)
(52) U.S. Cl. ................................... 536/23.1
(58) Field of Classification Search .............. None
See application file for complete search history.

(56) References Cited

U.S. PATENT DOCUMENTS 6,495,661 B1 * 12/2002 Glisson et al. .............. 530/300

OTHER PUBLICATIONS

Kroll et al 1993 DNA and Cell Biology vol. 12 No. 1993 pp. 441-453.*
Colman et al. (Research in Immunology 145: 33-36, 1994.*
Wall, 1996 Theriogenology, vol. 45, pp. 57-68.*
Houdebine, 1994, J. Biotech. vol. 34, pp. 269-287.*
Kappell, 1992, Current Opinions in Biotechnology, vol. 3, pp. 548-553.*
Cameron, 1997, Molec. Biol. 7, pp. 253-265.*
Niemann, 1998, Transg. Res. 7, pp. 73-75,.*
Mullins (1993, Hypertension, vol. 22, pp. 630-633.*
Mullins (1990, Nature, vol. 344, 541-544).*
Hammer (1990, Cell, vol. 63, 1099-1112).*
Mullins, 1989, EMBO J., vol. 8, pp. 4065-4072.*
Taurog, 1988, Jour. Immunol., vol. 141, pp. 4020-4023.*
Mullins (1996, J. Clin. Invest. vol. 98, pp. S37-S40).*
Luo et al. "Sequence analysis of *Pasteurella multocida* major outer membrane protein (OmpH) and application of synthetic peptides in vaccination of chickens against homologous strain challenge." *Vaccine* vol. 17. 1999. pp. 821-831.
Carter et al. "Pasteurellosis: Pasteurella multocida and Pasteurella hemolytica." *Advances in Veterinary Science, vol. 11, Academic Press, NY/London.* 1967. pp. 321-379.
Loosmore et al. " Outer Membrane Protein D15 is conserved among *Haemophilus influenzae* Species and May Represent a Universal Protective Antigen against Invasive Disease." *Infection and Immunity.* vol. 65. No. 9. 1997. pp. 3701-3707.
Bowland et al. "Bovine respiratory disease: Commercial vaccines currently available in Canada." *Can Vet.* Vol. 41. 2000. pp. 33-48.
Boyce et al. "Acapsular *Pasteurella multocida* B:2 Can Stimulate Protective Immunity against Pasteurellosis." *Infection and Immunity.* vol. 69. No. 3. 2001. pp. 1943-1946.

* cited by examiner

*Primary Examiner*—Robert A. Zeman
*Assistant Examiner*—Nina A Archie
(74) *Attorney, Agent, or Firm*—Merchant & Gould P.C.

(57) ABSTRACT

Disclosed is a recombinant vaccine for porcine atrophic rhinitis. A vaccine is provided which uses a *Pasteurella multocida* (D:4) outer membrane protein H. The vaccine uses a small size of peptides, so that it exhibits a remarkable activity. In addition, it is possible to provide a vaccine that can be applied in the body through a variety of routes.

6 Claims, 16 Drawing Sheets

FIG. 1

Figure 2:
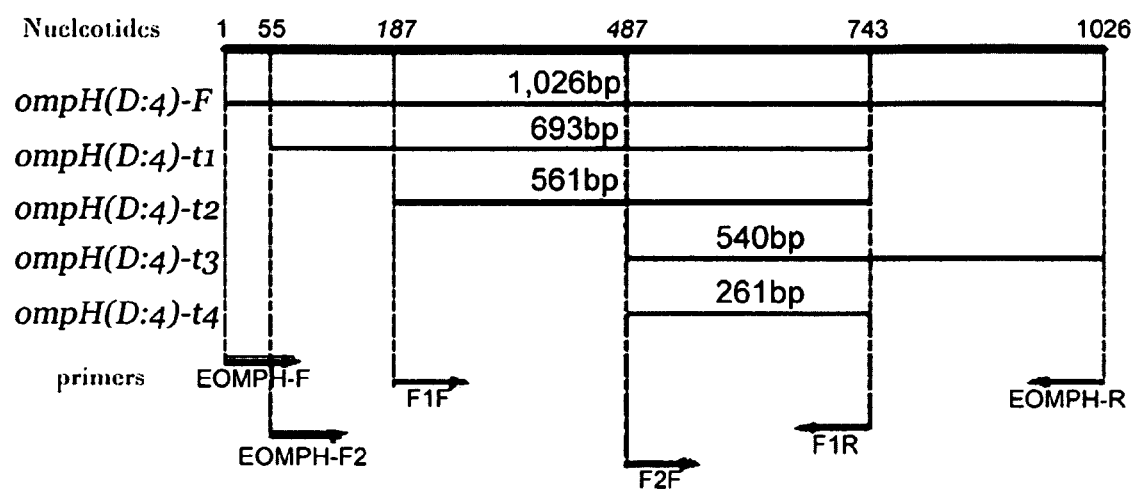

```
┌─────────────────────────────────────────────────────────────┐
│  FULL & TRUNCATED ompH (D:4) GENE CLONING THROUGH PCR       │
└─────────────────────────────────────────────────────────────┘
                              ↓
┌─────────────────────────────────────────────────────────────┐
│       PREPARING EXPRESSION VECTORS OF THE ABOVE GENES       │
└─────────────────────────────────────────────────────────────┘
                              ↓
┌─────────────────────────────────────────────────────────────┐
│       REFINING EXPRESSION PROTEINS OF THE ABOVE GENES       │
└─────────────────────────────────────────────────────────────┘
                              ↓
┌─────────────────────────────────────────────────────────────┐
│  IMMUNIZING THE MOUSE HAVING THE ABOVE PROTEIN AS AN ANTIGEN│
└─────────────────────────────────────────────────────────────┘
                              ↓
┌─────────────────────────────────────────────────────────────┐
│  IMMUNITY ASSAY WITH Pasteurella multocida(D:4) LIVE BACILLI│
└─────────────────────────────────────────────────────────────┘
```

FIGURE 8

Lane M: λDNA/HindIII
Lane 1,2: Genomic DNA of *Pasteurella multocida* (D:4)

Lane M: 1kb ladder marker
Lane 1: pET 32a / ompH(D:4)-F
Lane 2: BamH I and HindIII restriction enzyme digestion of pET32a / ompH(D:4)-F

FIG. 15

| Group | Absorbance ($A_{600}$) | CFU/ml | Dose ($\mu l$) | Number of live mice | | | | Mortality (%) |
|---|---|---|---|---|---|---|---|---|
| | | | | Day0 | Day1 | Day2 | Day3 | |
| I | 1.53 | $1.56 \times 10^3$ | 200 | 4 | 2 | 1 | 0 | 100 |
| II | 1.53 | $1.56 \times 10^3$ | 150 | 4 | 1 | 1 | 1 | 75 |
| III | 1.53 | $1.56 \times 10^3$ | 100 | 4 | 2 | 1 | 1 | 75 |
| IV | 1.53 | $1.56 \times 10^3$ | 75 | 4 | 1 | 1 | 1 | 75 |
| V | 1.53 | $1.56 \times 10^3$ | 50 | 4 | 3 | 2 | 2 | 50 |

FIG. 16

| Immunogen | Dose (μg) | $LD_{50}$ of pathogen (CFU/mℓ) | Number of live mice | | | | Mortality (%) | Protection (%) |
|---|---|---|---|---|---|---|---|---|
| | | | Day0 | Day1 | Day2 | Day3 | | |
| Recombinant OmpH(D:4)-F | 50 | $1.56 \times 10^3$ | 8 | 7 | 4 | 1 | 87.5 | 12.5 |
| Recombinant OmpH(D:4)-t1 | 50 | $1.56 \times 10^3$ | 9 | 8 | 5 | 1 | 88.9 | 11.1 |
| Recombinant OmpH(D:4)-t2 | 50 | $1.56 \times 10^3$ | 10 | 6 | 4 | 1 | 90 | 10 |
| Recombinant OmpH(D:4)-t3 | 50 | $1.56 \times 10^3$ | 10 | 7 | 4 | 2 | 80 | 20 |
| Recombinant OmpH(D:4)-t4 | 50 | $1.56 \times 10^3$ | 20 | 17 | 9 | 7 | 65 | 35 |
| Commercial vaccine | 50 | $1.56 \times 10^3$ | 9 | 8 | 8 | 4 | 55 | 45 |
| Inactivated vaccine | 50 | $1.56 \times 10^3$ | 8 | 7 | 5 | 2 | 75 | 25 |
| PBS | 0 | $1.56 \times 10^3$ | 10 | 10 | 7 | 1 | 90 | 10 |

RECOMBINANT VACCINE FOR PREVENTING AND TREATING PORCINE ATROPHIC RHINITIS

CROSS-REFERENCE TO RELATED APPLICATIONS

This application claims all benefits of Korean Patent Application No. 2007-9776 filed on Jan. 31, 2007 in the Korean Intellectual Property Office, the disclosures of which are incorporated herein by reference.

BACKGROUND OF THE INVENTION

1. Field of the Invention

The present invention relates to a recombinant animal vaccine. More particularly, the invention relates to a recombinant vaccine for preventing and treating porcine atrophic rhinitis. The invention provides a recombinant vaccine for porcine atrophic rhinitis using an outer membrane protein H (D:4) (OmpH (D:4)) of *Pasteurella multocida* (D:4).

2. Description of the Prior Art

The *Pasteurella multocida*, which is anaerobic gram-negative bacteria, is pathogenic bacterium causing a contagious disease that leads to a high economical loss for the livestock such as pig, birds and the like. The *Pasteurella multocida* is classified into 5 capsular serogroups (A, B, C, D, E, F) and 16 serotypes and D:4 is known to cause the porcine atrophic rhinitis (see Carter, G. R. 1967. *Pasteurella multocida* and *Pasteurella haemolytica*. Adv. Vet. Sci. Comp. Med. 11: 321-379). Most of the vaccines for the porcine atrophic rhinitis are vaccines using a small amount of *Pasteurella multocida* live or killed bacteria that are mainly inactivation-treated. However, such vaccines have a disadvantage that they may potentially cause a disease. In addition, it is difficult to expect a heterologous cross protection effect (see Boyce JD, Adler B (2001) Acapsular *Pasteurella multocida* B:2 can stimulate protective immunity against pasteurellosis. Infect Immun. 69(3): 1943-1946). In the mean time, the outer membrane protein H is researched as an antigen of the most effective vaccine for the *Pasteurella multocida* and is expected to exhibit the cross vaccine effect of the various interspecies of the *Pasteurella multocida*. In particular, it is possible to prepare the vaccine only with the antigen determining portion of the outer membrane protein, thereby exhibiting the more excellent effect (see Loosmore, S. M., Y. P. Yang, D. C. Coleman, J. M. Shortreed, D. M. England, and M. H. Klein. 1997. Outer membrane protein D15 is conserved among *Haemophilus influenzae* species and may represent a universal protective antigen against invasive disease. Infect. Immun. 65: 3701-3707.).

It is reported that the economic loss of the farms due to the respiratory disease such as porcine atrophic rhinitis reaches $640 million in U.S. (see Bowland, S. L. and P. E. Shewen. 2000. Bovine respiratory disease: Commercial vaccines currently available in Canada. Can. Vet. J. 41: 33-48.). Therefore, it is needed to develop the vaccine effective against the *Pasteurella multocida* so as to prevent the economic loss and to protect the livestock industries.

The inventors cloned 5 divided genes of the outer membrane protein H of the *Pasteurella multocida* (D:4) and expressed and refined the protein thereof, thereby producing the antigen. Then, the inventors immunized the mouse with the antigen and injected the live bacteria of the *Pasteurella multocida* (D:4) into the mouse, thereby performing the immunity investigation. In addition, the inventors compared the result thereof with the commercial porcine atrophic rhinitis vaccine and confirmed that the recombinant vaccine of the invention exhibited the higher survival rate, as compared to the conventional vaccine.

SUMMARY OF THE INVENTION

Accordingly, the present invention has been made to solve the above problems occurring in the prior art.

An object of the invention is to provide a vaccine for porcine atrophic rhinitis containing recombined *Pasteurella multocida* (D:4) outer membrane protein H (D:4).

Another object of the invention is to provide a method of preparing a vaccine for porcine atrophic rhinitis containing recombined *Pasteurella multocida* (D:4) outer membrane protein H (D:4).

In order to achieve the above objects, there is provided a gene having any one base sequence of sequence Nos. 7 to 11 and coding a protein that is immunogenic to *Pasteurella multocida* (D:4).

According to an embodiment of the invention, there is provided a recombinant expression vector comprising the above gene.

According to an embodiment of the invention, there is provided a host cell transformed with the above recombinant expression vector.

According to an embodiment of the invention, there is provided a recombinant vaccine comprising, as an antigen, a protein expressed from the above recombinant expression vector or recombinant outer membrane protein H of *Pasteurella multocida* (D:4) strain coded by a gene having any one sequence of sequence Nos. 7 to 11 or piece thereof.

According to an embodiment of the invention, there is provided a method for preventing or treating a disease comprising administrating a protein expressed from the above recombinant expression vector having an effective amount or recombinant outer membrane protein H of *Pasteurella multocida* (D:4) strain coded by a gene having any one sequence of sequence Nos. 7 to 11 or piece thereof to a subject for which it is necessary to prevent or treat a disease due to the *Pasteurella multocida* (D:4) strain.

The term "outer membrane protein H (OmpH)" used in the specification including the claims means one of porin proteins serving as a passage in an outer membrane of *Pasteurella multocida* (D:4). In the specification, the gene coding the outer membrane protein H of *Pasteurella multocida* (D:4) is indicated as ompH (D:4) (outer membrane protein H (D:4) gene) and the protein coded by ompH (D:4) is indicated as OmpH (D:4).

In order to achieve the above objects, the inventors investigated the whole genes of the outer membrane protein H of *Pasteurella multocida* (D:4) from a BLAST sequence database (National Center for Biotechnology Information, National Library of Medicine, Bethesda, Md., U.S.A.) and prepared EOMPH-F (sequence No. 1), EOMPH-F2 (sequence No. 2), F1F (sequence No. 3), F2F (sequence No. 4), F1R 9 (sequence No. 5) and EOMPH-R (sequence No. 6) primers. The inventors cloned 5 (five) divided genes and expressed and refined the protein thereof, thereby producing an antigen. Then, the inventors immunized the mouse with the antigen and injected the live bacteria of the *Pasteurella multocida* (D:4) into the mouse, thereby performing the immunity investigation. In addition, the inventors compared the result thereof with the commercial porcine atrophic rhinitis vaccine and confirmed that the recombinant vaccine of the invention exhibited the higher survival rate, as compared to the conventional vaccine.

For the effective in vivo prevention and anti-infective actions, the OmpH protein may be singularly administrated or may be administrated with an appropriate pharmaceutical carrier. The vaccine may be administrated in an oral, parenteral, endonasal or intravenous manner. The factors relating to the dose of the vaccine may include, for example ages, weights and maternal antibody levels of infected poultry. The vaccine of the invention may be administrated in a variety of doses. The OmpH protein may be mixed with pharmaceutically acceptable inactive adjuvants, such as lactose, starch, calcium carbonate and sodium citrate, and buffer agent to formulate it in a tablet or capsule shape and the like. The mixture may be also powdered or suspended in an aqueous solution so that the powders and solution agent can be applied to the feed or drinking water. In order to promote the oral intake of the vaccine, a variety of known agents may be used to appropriately sweeten or to provide the vaccine powders or solution with the flavouring. For the parenteral administration, the OmpH protein may be mixed with the pharmaceutically acceptable carrier(s) that is well known in the art, such as physiological saline, water, propylene glycol and the like. In such a way, the vaccine can be administrated in a parenteral, endonasal or oral manner by the method well known in the veterinary science field. The recombinant vaccine of the invention may be administrated in an intravenous manner by a syringe. In this case, the vaccine of the invention is mixed with a pharmaceutically acceptable aqueous carrier such as physiological saline. The formulation of the vaccine for the parenteral and intravenous administration may further comprise an emulsifying agent or suspension agent together with the pharmaceutically acceptable diluting agent for adjusting the transfer and the vaccine dose.

BRIEF DESCRIPTION OF THE DRAWINGS

The above and other objects, features and advantages of the present invention will be more apparent from the following detailed description taken in conjunction with the accompanying drawings, in which:

FIG. 1 schematically shows an entire process according to an embodiment of the invention;

FIG. 2 shows a primer used to clone the portions used as a peptide vaccine according to an embodiment of the invention;

FIG. 3 is a map of a pET32a/ompH(D:4)-F vector that is a recombinant vector according to an embodiment of the invention;

FIG. 4 is a map of a pRSET B/ompH(D:4)-t1 vector that is a recombinant vector according to an embodiment of the invention;

FIG. 5 is a map of a pRSET B/ompH(D:4)-t2 vector that is a recombinant vector according to an embodiment of the invention;

FIG. 6 is a map of a pRSET B/ompH(D:4)-t3 vector that is a recombinant vector according to an embodiment of the invention;

FIG. 7 is a map of a pRSET B/ompH(D:4)-t4 vector that is a recombinant vector according to an embodiment of the invention;

FIG. 8 shows a result of analyzing, in agarose gel, a separation result of DNA from *Pasteurella multocida* (D:4);

FIG. 9 shows a result of PCR using the primer shown in FIG. 2;

FIG. 10 shows a result that ompH(D:4)-F, which is a full length (F) ompH(D:4) gene, is inserted in pET32a, which is *Escherichia coli* expression vector;

FIG. 11 shows a result that each ompH(D:4) gene truncated (t), which will be used as a peptide vaccine, is inserted in pRSET B, which is *E. coli* expression vector;

FIG. 12 shows a result of analyzing a result, which ompH (D:4) gene is expressed through *E. coli* BL21 (DE3), using SDS-PAGE;

FIG. 13 shows a process of immunizing the mouse using each OmpH (D:4) protein as an antigen;

FIG. 14 shows an ELISA analysis of serum collected from each mouse immunized;

FIG. 15 shows an analysis result of $LD_{100}$, after active *Pasteurella multocida* (D:4) live bacteria are injected in the immunized mouse for each concentration, so as to verify a level of immunization; and FIG. 16 shows an analysis result of a survival rate of the mouse using the $LD_{100}$ values, after active *Pasteurella multocida* (D:4) live bacteria are injected in the immunized mouse.

DETAILED DESCRIPTION OF THE PREFERRED EMBODIMENTS

Hereinafter, the specific constitution and actions of the invention will be described with reference to embodiments. However, it should be noted that the embodiments and experimental examples are provided to exemplify the invention, not limit it.

Embodiments

Embodiment 1

OmpH(D:4) Gene Amplification (First Step) PCR Amplification of OmpH(D:4)-F and Each of Truncated OmpH(D:4) Genes The ompH(D:4) genes, which were already known, were investigated from the BLAST sequence database (National Center for Biotechnology Information, National Library of Medicine, Bethesda, Md., U.S.A.) to prepare EOMPH-F (sequence No. 1), EOMPH-F2 (sequence No. 2), F1F (sequence No. 3), F2F (sequence No. 4), F1R 9 (sequence No. 5) and EOMPH-R (sequence No. 6) primers, which included the restriction enzyme recognition portion (BamHI, HindIII) (refer to FIG. 2). As template DNA, the strain cultured in BHI culture medium was boiled for 5 minutes and then the upper layer solution 5 μl was used. In addition, a reaction mixture solution 20 μl of 10 mM Tris-HCl (pH 8.4), 50 mM KCl and 3 mM $MgCl_2$, Super Taq DNA polymerase 1 μl (SuperBio, Korea), 2 mM dNTP and each primer 10 pmol were used. As a result, DNA pieces of various sizes, ompH(D:4)-F (sequence No. 7), ompH(D:4)-t1 (sequence No. 8), ompH(D:4)-t2 (sequence No. 9), ompH(D:4)-t3 (sequence No. 10) and ompH(D:4)-t4 (sequence No. 11) were obtained.

(Second Step) Cloning of OmpH(D:4) Genes having Various Sizes

The respective 5 (five) ompH(D:4) gene pieces amplified with PCR were gel-extracted from 0.8% agarose gel (Qiagen, U.S.A.), inserted into PGEM-T® easy vector (Promega, U.S.A.) using T4 DNA ligase (Takara, Japan) and transformed into *E. coli* DH5α strain according to a heat shock method. The transformed strain was cultured in 1.5% LB ampicillin (50 μg/Ml) agar plate. Then, white colony only was selected through the α-complementation selection to secure 5 (five) types of recombinant plasmids.

Embodiment 2

Figure 3:
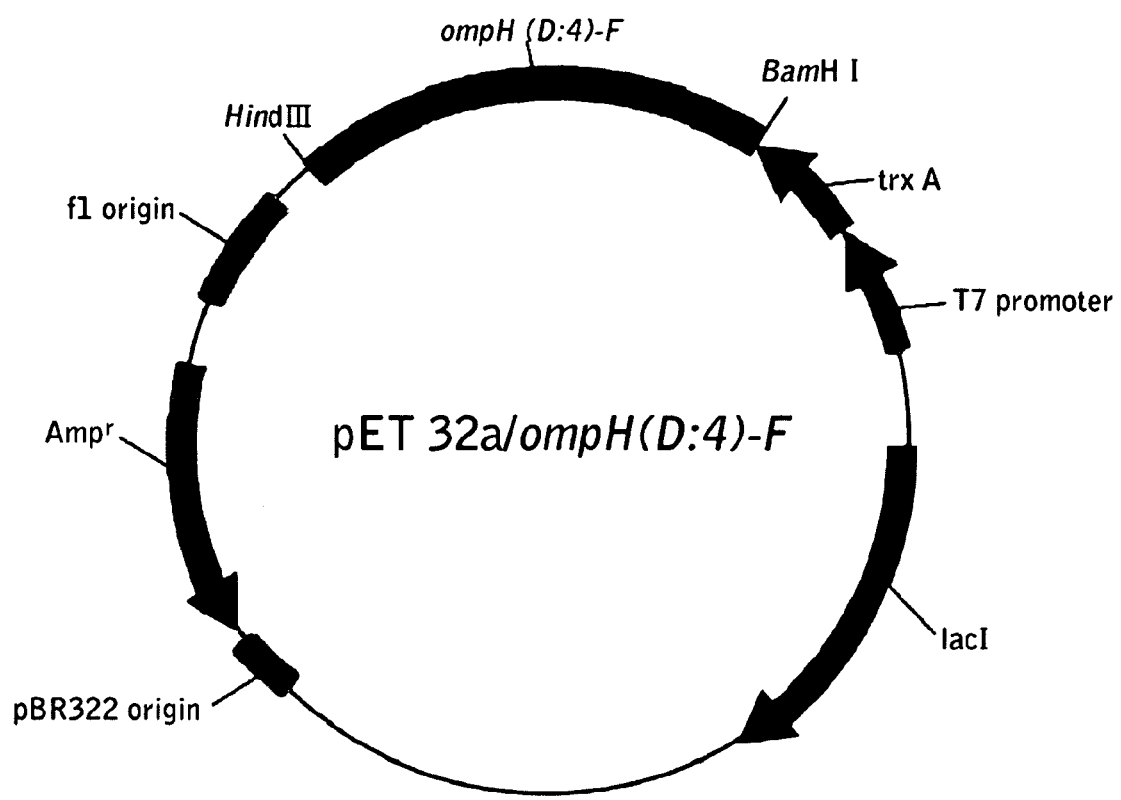
Figure 4:
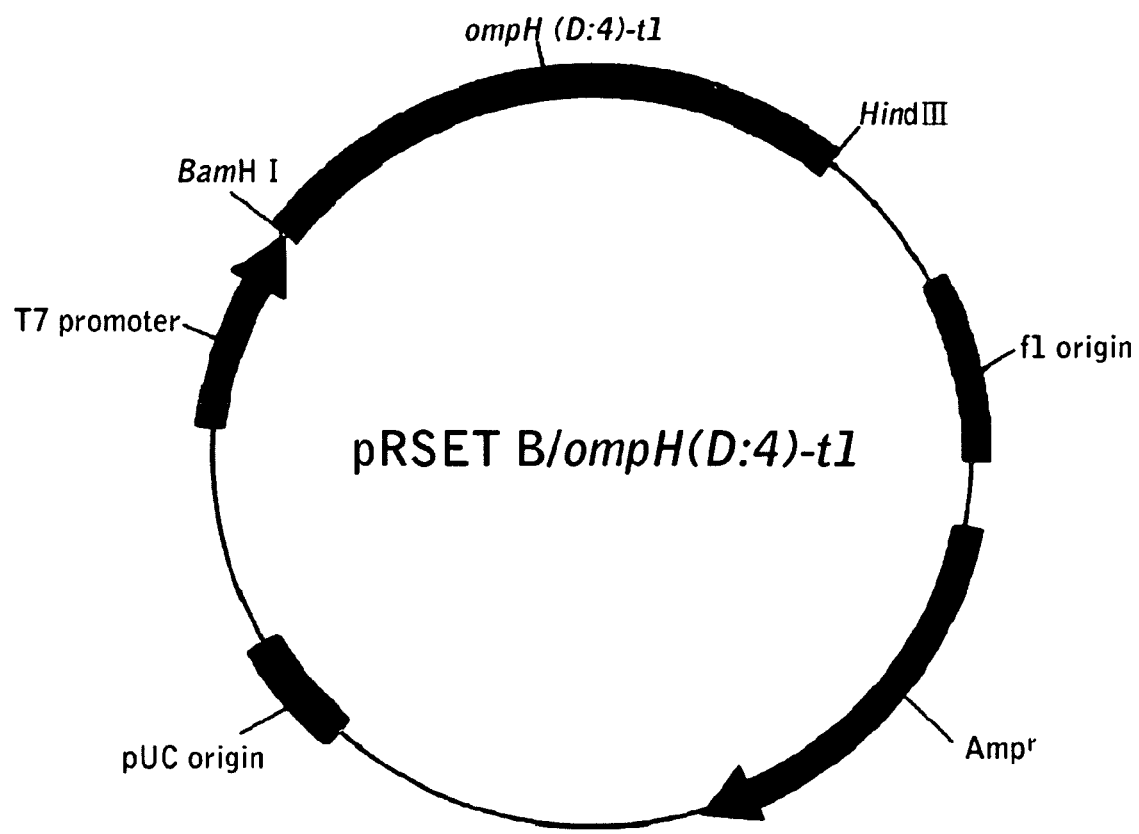
Figure 5:
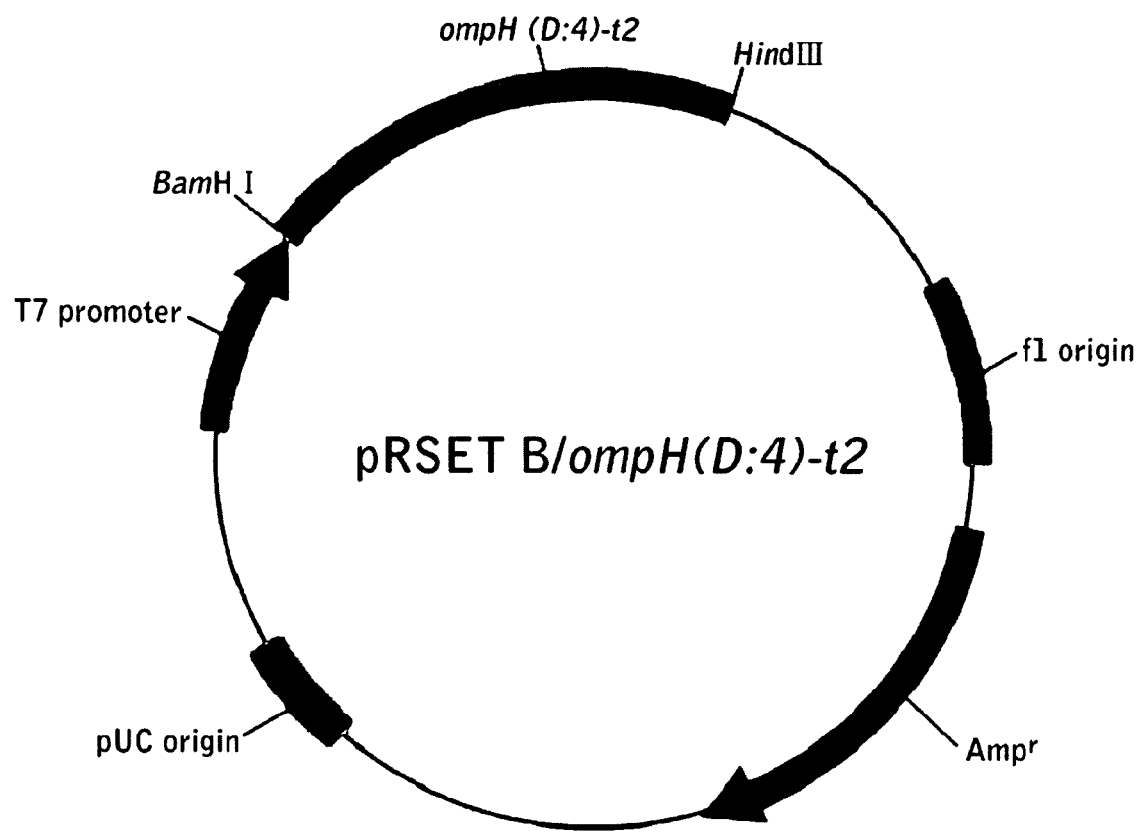
Figure 6:
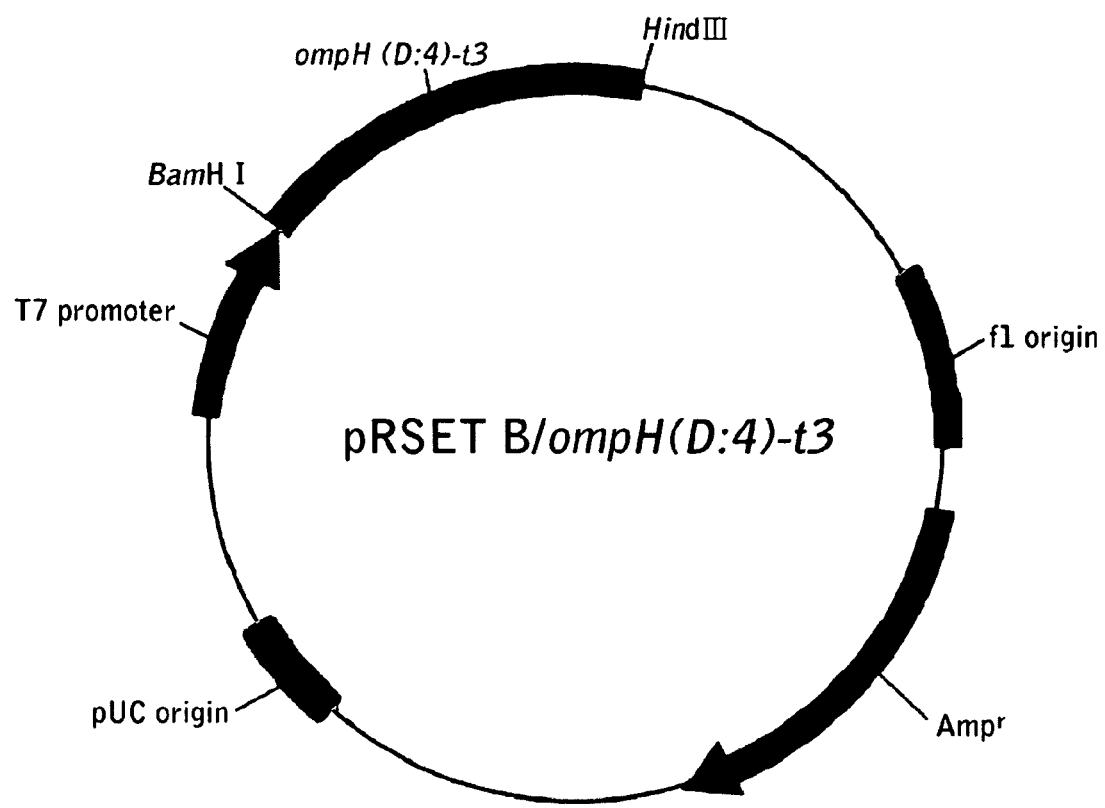
Figure 7:
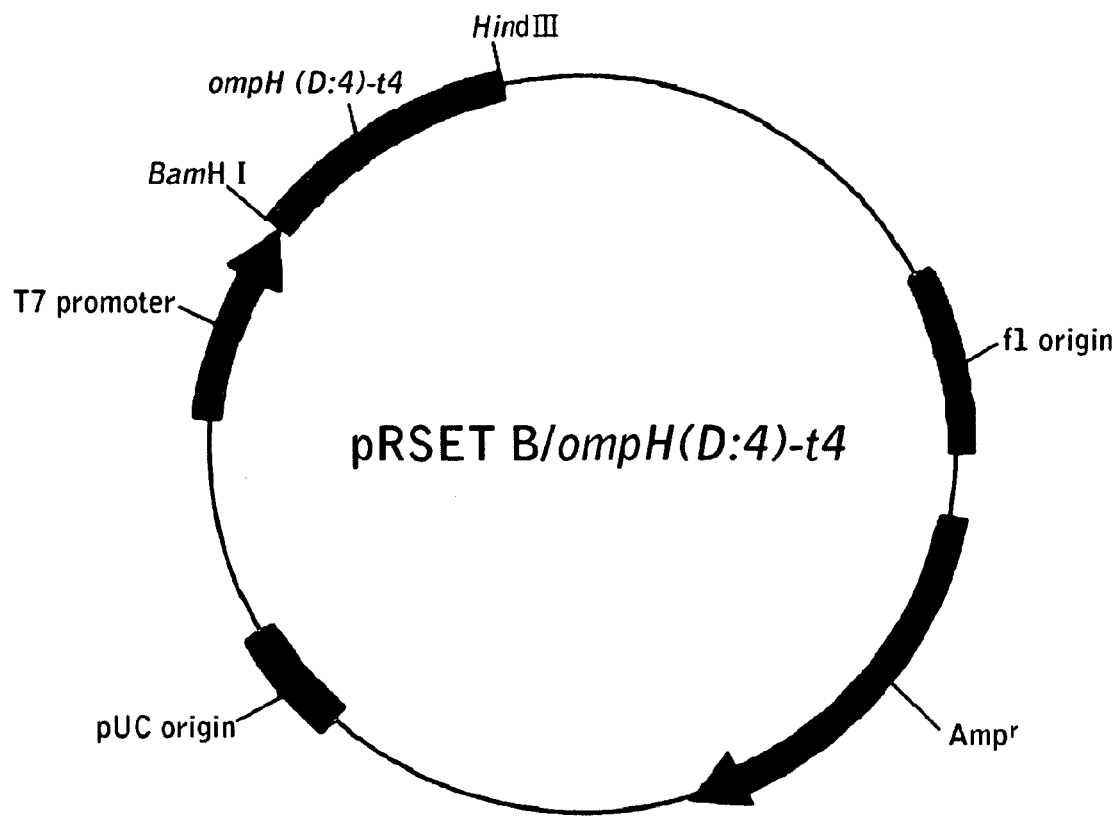
Figure 9:
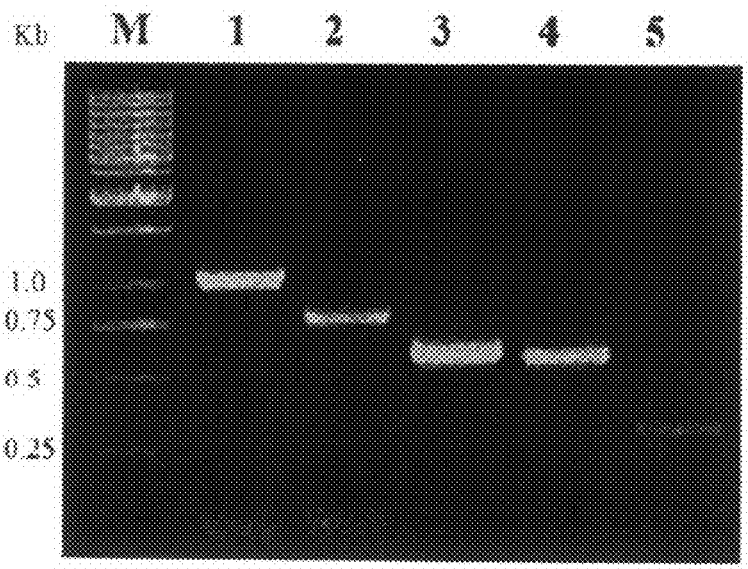
Figure 10:
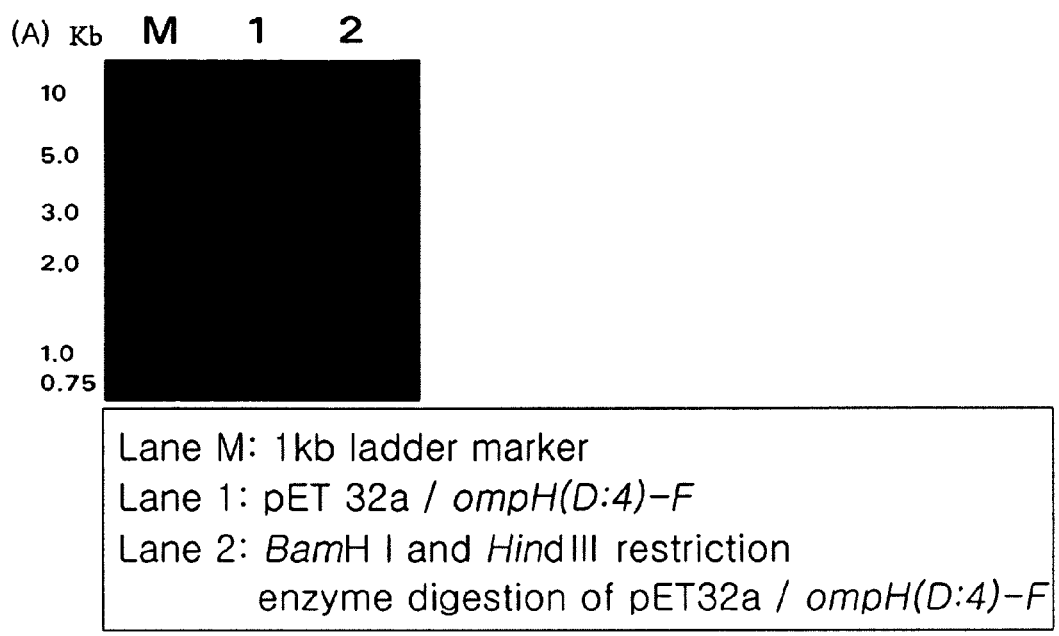
Figure 11:
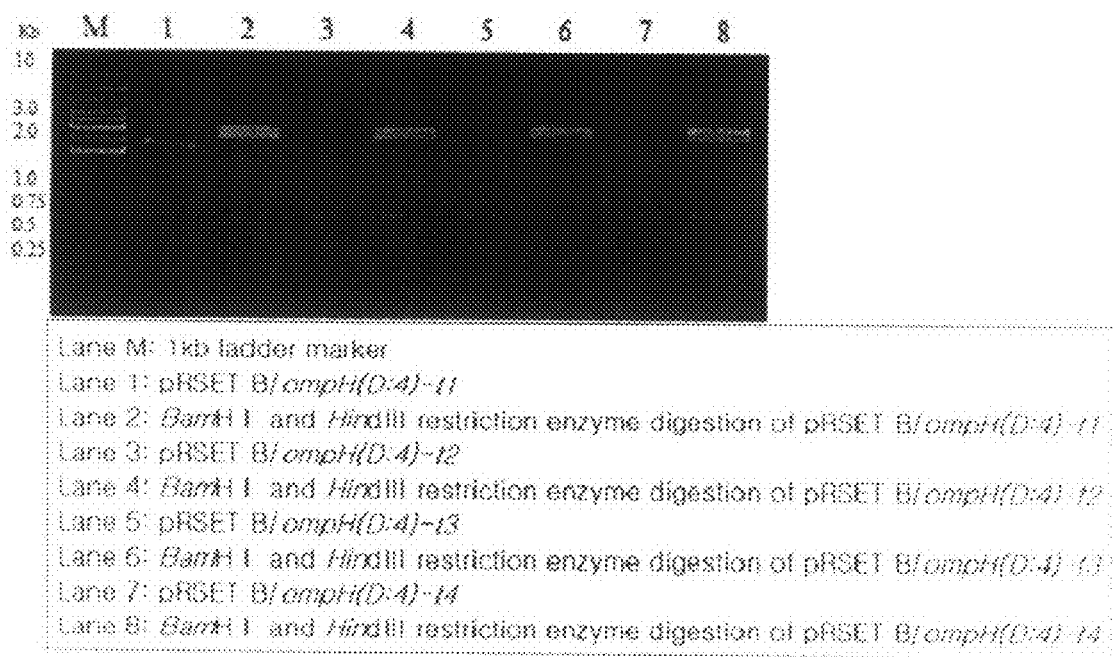
Figure 12:
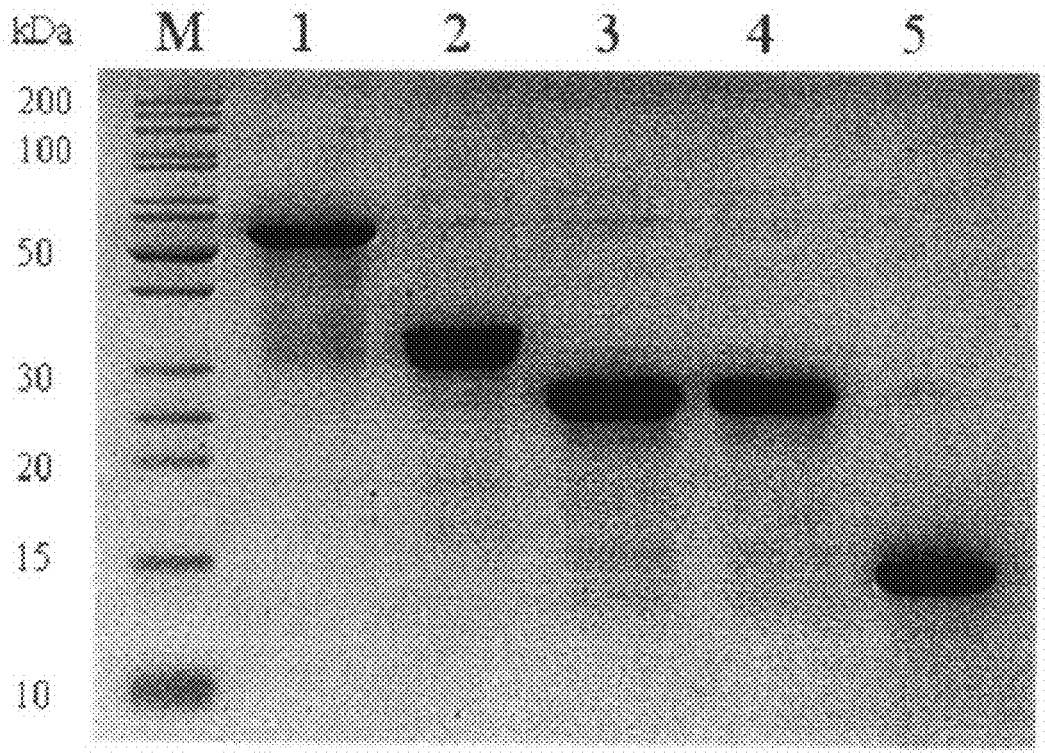
Figure 13:
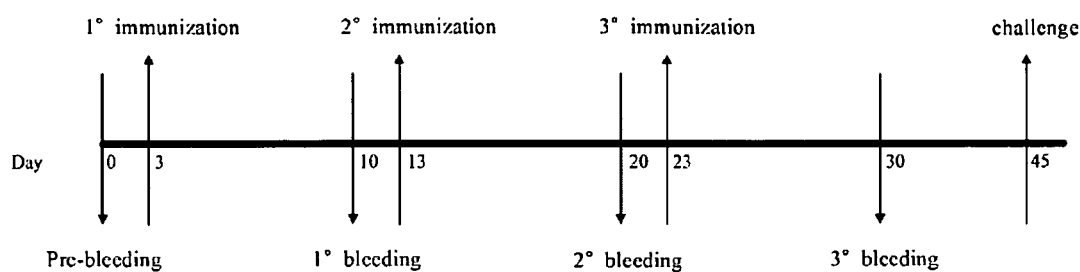
Figure 14:
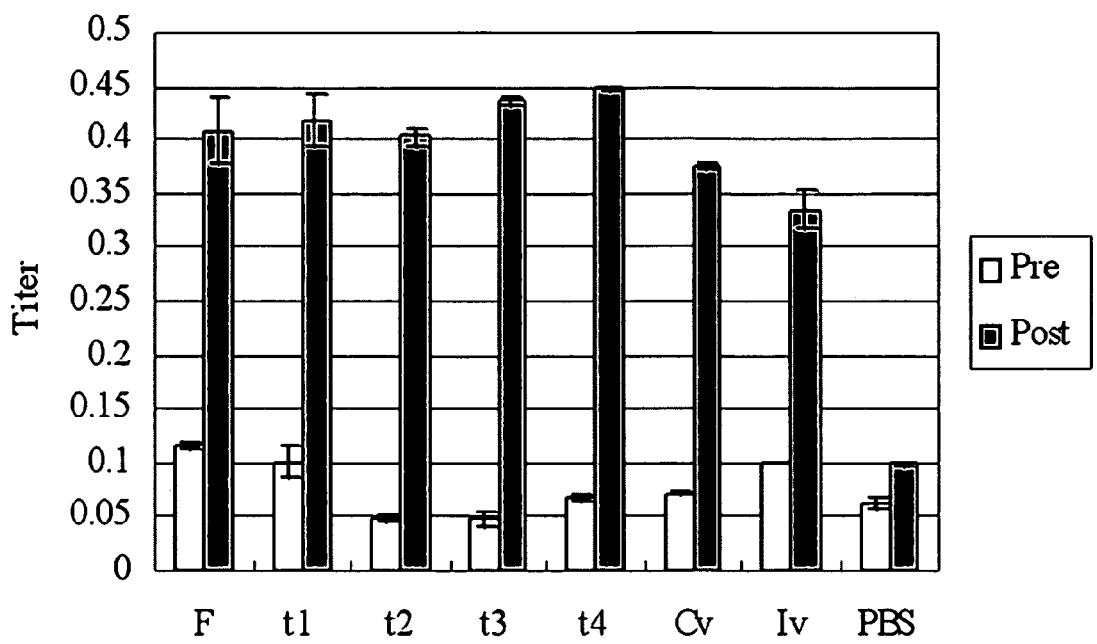

Expression and Refinement of OmpH (D:4) protein (First Step) Preparation of Recombinant *E. coli* Expression Vector of OmpH(D:4) Gene The ompH (D:4)-F, t1, t-2, t-3 and t-4 DNA pieces, which were cloned to PGEM-T® easy prepared in the embodiment 1, were subcloned to pET32a or pRSET B expression vector (Invitrogen, U.S.A.) treated with BamHI and HindIII to prepare pET32a/ompH (D:4)-F (FIG. 3), pRSET B/ ompH (D:4) t1 (FIG. 4),), pRSET B/ ompH(D:4)-t2 (FIG. 5), pRSET B/ ompH(D:4)-t3 (FIG. 6) and) and pRSET B/ ompH(D:4)-t4 vectors (FIG. 7). The pET32a and pRSET B vectors are vectors that are made to have the 6 (six) histidine coding portions at N-terminal portion so as to enable the Ni-NTA resin to be easily used in refining the protein.

(Second Step) OmpH Protein Expression

The pET32a/ompH(D:4) vector was transformed into *E. coli* BL21(DE3) strain (Novagen, Germany) and then the selection was performed in the 1.5% LB agar plate. The produced colony was inoculated to the 1L LB culture medium to which ampicillin (50 μg/ml) was added and then cultured up to the exponential growth phase ($A_{600}$=0.5, Ultrospec 2000, Pharmacia, U.S.A.) in the 37° C. stirring incubator. 0.5 mM isopropyl-β-D-thiogalactopyranoside (IPTG) was induced at 34° C. and cultured in the strong stirring incubator for one night, so that OmpH protein was expressed. As the control group, the 0 hr (before the IPTG induction) strain and the o/n (after the culture for one night) strain were separately prepared by 1 ml. The strain 10,000 g, which was cultured for one night, was centrifugally separated at 4° C. for 20 minutes (J2-21M/E, Beckman, U.S.A.). The strain, which was separated so as to separate the protein, was dissolved in the dissolved buffer of pH 8.0 ml per strain 1 g, which was comprised of 50 mM $Na_2PO_4$, 300 mM NaCl and 10 mM imidazole. The suspended strain was repeatedly subject to the sonication by repeating 5 seconds bursting and 9 seconds braking processes for 5 minutes and the dissolved matter 10,000 g was centrifugally separated at 4° C. for 20 minutes, so that the supernatant liquid and the pellets were separated. The separated pellets were stirred in the dissolved buffer of pH 8.0 for one night, which was comprised of 100 mM $NaH_2PO_4$, 10 mM Tris-Cl and 8M urea, so as to separate the fat-soluble denaturing condition protein from the other materials and 10,000 g was centrifugally separated at 4° C. for 20 minutes to secure the supernatant liquid.

(Third Step) Refinement of OmpH (D:4) Protein

In order to refine the respective OmpH proteins, nickel-nitrilotriacetic acid (Ni-NTA) resin (Qiagen, Germany) was used. The separated denaturing condition OmpH (D:4) protein suspension was put in a column and then was subject to a reaction at 4° C. for about 12 hours so that the Ni-NTA resin and the expressed OmpH protein could be connected. After taking the sample, the denaturing condition wash buffer 5 ml (100 mM $NaH_2PO_4$, 10 mM Tris-Cl, 8M urea, pH 6.3) was added in the column and was subject to the reaction three times for every 30 minutes, so that the unnecessary proteins were removed. Then, the denaturing condition elution buffer 3 ml (100 mM $NaH_2PO_4$, 10 mM Tris-Cl, 8M urea, pH 4.5) was put in the column and was subject to the reaction two times for every 1 hour and 30 minutes, so that the proteins connected to the resin were separated. In order to check the band formation of the secured samples, the samples were sampled using 1% sodium dodecyl sulfate and then checked through the polyacrylamide gel electrophoresis.

(Fourth Step) Quantitative Analysis of Recombinant OmpH (D:4) Antigen

The concentrations of the respective OmpH(D:4) refined were measured with a Bradford analysis. The OmpH(D:4) antigen 20 μl was added to the Bradford assay solution 200 μl (Bio-rad, U.S.A.), in which the distilled water 780 μl was then put. In order to reduce the standard deviation, the sample 200 μl was divided to three wells of 96 well plates (Costar, Corning Co., NY, U.S.A.) As the control group, the bovine serum albumin (BSA, Sigma, U.S.A.) was subject to the serial dilution from the undiluted solution to $1/2^6$ concentration by 1/2 and the PBS was put in the last well. The concentrations were measured at UV 595 nm.

Embodiment 3

Anti-OmpH(D:4) Antigen Production from the Mouse and Immunity Assay (First Step) Anti-OmpH(D:4) Antigen Production from the Mouse The respective OmpH(D:4) proteins refined as the immunogen were injected to the mouse to secure the OmpH(D:4) immune serum. The 90 (ninety) female albino ICR mice of 5 to 7 weeks were randomly classified into OmpH (D:4)-F group, OmpH (D:4)-t1 group, OmpH (D:4)-t2 group, OmpH (D:4)-t3 group, OmpH (D:4)-t4 group, commercial vaccine group, inactivated vaccine group and PBS injected group. Each group consisted of 10 mice, except that the OmpH(D: 4)-t4 group consisted of 20 mice. From each mouse, the immune serum was separated. After three days, each OmpH (D:4) antigen 50 μg and Freund's complete adjuvant (FCA, Sigma, U.S.A.) having the same amount were intraperitoneally injected. As the positive control group, the formalin-killed whole cell of *Pasteurella multocida* (D:4), whose activity was not verified when it reached the nutrient culture medium, and the commercial vaccine were mixed with the FCA in the same amount and then injected. As a negative control group, the mixture of the PBS and the same amount of FCA was injected. After one week, all the mice were eye-bled and the whole blood 100 μl was secured from each mouse and reserved at 4° C. for 6 hours to induce the blood coagulation. Then, it was centrifugally separated at 3,000 rpm for 20 minutes to remove the blood corpuscles, so that the primary serum was obtained. The secondary immunization was carried out after ten days from the primary immunization. Again, the blood was collected after 7 days to secure the secondary serum.

(Second Step) ELISA Analysis for the Produced Sera

The titer of the immune globulin was measured through the ELISA. Each of the refined OmpH(D:4) recombinant proteins 5 ml was mixed with the coating buffer and 100 μl, per each well was put in the 96 well plates, which were then subject to the reaction at 37° C. for 1 hour. The PBS 200 μl (PBST; Tween-20 (trademark), Dae-Jung, Korea), in which polyoxyethylene sorbitan monolaurate 0.05% was mixed, was used to wash each well. Then, the solution 200 μl, in which 3% BSA was added to the PBST, was divided in each well and was subject to the reaction at 4° C. for 16 hours. In order to prepare the primary antibody, the PBS, in which 1% BSA was dissolved, and the antiserum, which was diluted to 1/1,000, were mixed. Then, the mixture 100 μl was divided in each well and subject to the reaction at 37 (C. for 1 hour, which were then washed five times with the PBST 200 μl. The pre-serum sample was diluted to 1/100 before using. As the secondary serum, the sample 100 μl, in which the horseradish peroxidase-conjugated goat anti-mouse IgG (Sigma, U.S.A.)

was diluted to 1/10,00 together with the PBST, was divided in each well and was subject to the reaction at 37 (C. for 1 hour, which were then washed five times with the PBST. In the last step, the 3,3',5,5'-tetramethylbenzidine (TMB) sample, which was dissolved in the dimethyl sulfoxide (DMSO), was mixed with the phosphate-citrate in a ratio of 1:10. The mixture 10 µl was divided in each well and subject to the reaction for 30 minutes. Then, the absorbency was measured at 650 nm.

(Third Step) Immunity Assay for the Mouse of the Analyzed Antigen

In order to set a condition of 100% lethal dose (LD100) of Pasteurella multocida (D:4) having an activity, 25 wild mousse mice, which were not immunized, were randomly divided into 5 cages. The activated strains, which exhibited 1.53 O.D. at A600, 200 µl, 100 µl, 70 µl and 50 µl were injected in the mousse mice of each cage with I.P., and the progress was observed for 3 days. In order to check a level immunized with OmpH (D:4), the strain having an activity of $LD_{100}$ was injected in the mice of the eight groups having produced the antigens, which were then observed for 7 days. Then, the survival rate thereof was checked.

Results

According to the immunity assay result for the mice, all the OmpH (D:4)-F, OmpH (D:4)-t1, OmpH (D:4)-t2, OmpH (D:4)-t3 and OmpH (D:4)-t4 exhibited the immunity for Pasteurella multocida (D:4). The immunity of OmpH(D:4)-t4 was most excellent, exhibited the immunity better than the inactivated vaccine and also exhibited the vaccine effect similar to the commercial vaccine although it was a little worse than the commercial vaccine. In other words, the vaccine effect of OmpH(D:4) was confirmed as the peptide vaccine for the porcine atrophic rhinitis.

Preparation Example of the Vaccine Composition

For the effective in vivo prevention and anti-infective actions, the vaccine composition of the invention may be individually administrated in a form of the OmpH protein. Alternatively, the vaccine composition may be administrated together with the pharmaceutical carrier suitable for the poultry. An example of the vaccine composition is as follows.

| | |
|---|---|
| Refined OmpH (D:4) of 0.5 mg/ml | 100 µl |
| Freund's Complete Adjuvant | 100 µl |

As described above, the peptide vaccine using the outer membrane protein H (D:4) uses a small size of peptides, so that it increases the efficiency thereof and little exhibits an incidence possibility. In addition, the conventional vaccine is administrated in a form of the injection only. However, in addition to the injection, the peptide vaccine of the invention is expressed in the crops to be used for the feed of the pig, thereby exhibiting the vaccine effect. Alternatively, the peptide vaccine may be sprayed on the pig to exhibit the vaccine effect through the immune reaction of the mucous membrane. Like this, the peptide vaccine can be used to immunize the pig in a variety of manners.

While the invention has been shown and described with reference to certain preferred embodiments thereof, it will be understood by those skilled in the art that various changes in form and details may be made thereto without departing from the spirit and scope of the invention as defined by the appended claims.

What is claimed is:

1. An isolated polynucleotide comprising the nucleotide selected from the group consisting of the sequence of SEQ ID NOs: 7-11, the polynucleotide sequence encoding a polypeptide that is antigenic and induces an immunogenic response to *Pasteurella multocida* (D:4) in a mammal.

2. A recombinant expression vector comprising the gene polynucleotide according to claim 1.

3. The recombinant expression vector according to claim 2, wherein the expression vector is in a pET32a or pRSET B expression vector.

4. The recombinant expression vector according to claim 3, wherein the recombinant expression vector is a pRSET B expression vector.

5. An isolated host cell transformed with the recombinant expression vector according to claim 2.

6. The host cell according to claim 5, wherein the host cell is *Escherichia coli*.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: EOMPH-F

<400> SEQUENCE: 1
gggattgggg atcctatgaa aaaga                                           25

<210> SEQ ID NO 2
<211> LENGTH: 25
<212> TYPE: DNA
<213> ORGANISM: Artificial Sequence
<220> FEATURE:
<223> OTHER INFORMATION: EOMPH-F2

<400> SEQUENCE: 2
cagcggatcc agcaacagtt tacaa                                           25

<210> SEQ ID NO 3
<211> LENGTH: 24
<212> TYPE: DNA
<213> ORGANISM: Artificial Sequence
<220> FEATURE:
<223> OTHER INFORMATION: F1F

<400> SEQUENCE: 3

```
aaagcggatc ctgacttagg cgag                                              24

<210> SEQ ID NO 4
<211> LENGTH: 24
<212> TYPE: DNA
<213> ORGANISM: Artificial Sequence
<220> FEATURE:
<223> OTHER INFORMATION: F2F

<400> SEQUENCE: 4
ttcaaggatc cagaattcaa cggt                                              24

<210> SEQ ID NO 5
<211> LENGTH: 24
<212> TYPE: DNA
<213> ORGANISM: Artificial Sequence
<220> FEATURE:
<223> OTHER INFORMATION: F1R

<400> SEQUENCE: 5
agtcacttaa gcttgtgcgt agtc                                              24

<210> SEQ ID NO 6
<211> LENGTH: 25
<212> TYPE: DNA
<213> ORGANISM: Artificial Sequence
<220> FEATURE:
<223> OTHER INFORMATION: EOMPH-R

<400> SEQUENCE: 6
ctaacaaagc ttagaagtgt acgcg                                             25

<210> SEQ ID NO 7
<211> LENGTH: 1030
<212> TYPE: DNA
<213> ORGANISM: Artificial Sequence
<220> FEATURE:
<223> OTHER INFORMATION: OmpH-F
<220> FEATURE:
<221> NAME/KEY: misc_feature
<222> LOCATION: (6)..(8)
<223> OTHER INFORMATION: Start codon
<220> FEATURE:
<221> NAME/KEY: misc_feature
<222> LOCATION: (1028)..(1030)
<223> OTHER INFORMATION: Termination codon

<400> SEQUENCE: 7
atcctatgaa aaagacaatc gtagcatagc agtcgcagca gtagcagcaa cttcagcaaa       60
cgcagcaaca gtttacaatc aagacggtac aaaagttgat gtaaatggtt ctgtgcgttt      120
aatccttaaa aaagaaaaag ataaacgtgg tgatttagtg ataacggtt cacgcgtttc       180 tttcaaagca tctcatgact taggcgaggg cttaagtgcg ttagcttacg cagaactccg      240
tttcagtaca aagaggaag tagaagttac acaaaatcaa aaagtagttc gtaaatacaa       300
ggttgaacga attggtaacg atgttcatgc aaaacgtctt tatgcgggat cgcgtatga       360 aggtttaggt acattaactt tcggtaacca attaactatt ggtgatgatg ttggtgtgtc      420
tgactacact tacttcttgg gtggtattaa caaccttctt tctagcggtg aaaaagcaat      480
taacttcaag tctgcagaat tcaacggttt cacatttggt ggtgcttatg tcttctcagc      540
gggtgctgac aaacaagcag cacgtgacgt tcgcggtttc gttgtagcag gtttatacaa      600
cagaaaaatg ggtgatgttg gtcttgcact tgaagcaggc tatagccaag aatatgtaac      660
```

```
agaaacagcc aaacaagaaa aagaaaaagc ctttatggtc ggtactgaat tatcatatgc      720
aggtttagca ctaggtgttg actacgcaca atctaaagtg actaacgtag atggtaaaaa      780
acgtgcactt gaagtgggct taaactatga ccttaacgat aaagcgaaag tttacactga      840
tttgatttgg gcgaaaaaag gtccaaaagg tgcgactaca agagatcgcg ctatcatctt      900
aggtgcgggc tacaaacttc acaaacaagt tgaaacttt gttgaaggtg gttggggcag      960
aactaaaaaa gcagctggcg taacaactaa agataacaaa gttggcgttg gtttacgcgt     1020
acacttctaa                                                            1030

<210> SEQ ID NO 8
<211> LENGTH: 688
<212> TYPE: DNA
<213> ORGANISM: Artificial Sequence
<220> FEATURE:
<223> OTHER INFORMATION: OmpH-t1

<400> SEQUENCE: 8
atccacagtt tacaatcaag acggtacaaa agttgatgta aatggttctg tgcgtttaat       60
ccttaaaaaa gaaaaagata aacgtggtga tttagtggat aacggttcac gcgtttcttt      120
caaagcatct catgacttag gcgagggctt aagtgcgtta gcttacgcag aactccgttt      180
cagtacaaaa gaggaagtag aagttacaca aaatcaaaaa gtagttcgta atacaaggt       240 tgaacgaatt ggtaacgatg ttcatgcaaa acgtctttat gcgggattcg cgtatgaagg      300
tttaggtaca ttaactttcg gtaaccaatt aactattggt gatgatgttg gtgtgtctga      360
ctacacttac ttcttgggtg gtattaacaa ccttctttct agcggtgaaa aagcaattaa      420
cttcaagtct gcagaattca acggtttcac atttggtggt gcttatgtct tctcagcggg      480
tgctgacaaa caagcagcac gtgacggtcg cggtttcgtt gtagcaggtt tatacaacag      540
aaaaatgggt gatgttggtc ttgcacttga agcaggctat agccaagaat atgtaacaga      600
aacagccaaa caagaaaaag aaaaagcctt tatggtcggt actgaattat catatgcagg      660
tttagcacta ggtgttgact acgcacaa                                         688

<210> SEQ ID NO 9
<211> LENGTH: 560
<212> TYPE: DNA
<213> ORGANISM: Artificial Sequence
<220> FEATURE:
<223> OTHER INFORMATION: OmpH-t2

<400> SEQUENCE: 9
atcctgactt aggcgagggc ttaagtgcgt tagcttacgc agaactccgt ttcagtacaa       60
aagaggaagt agaagttaca caaaatcaaa aagtagttcg taaatacaag gttgaacgaa      120
ttggtaacga tgttcatgca aaacgtcttt atgcgggatt cgcgtatgaa ggtttaggta      180
cattaacttt cggtaaccaa ttaactattg gtgatgatgt tggtgtgtct gactacactt      240
acttcttggg tggtattaac aaccttcttt ctagcggtga aaaagcaatt aacttcaagt      300
ctgcagaatt caacggtttc acatttggtg gtgcttatgt cttctcagcg ggtgctgaca      360
aacaagcagc acgtgacggt cgcggtttcg ttgtagcagg tttatacaac agaaaaatgg      420
gtgatgttgg tcttgcactt gaagcaggct atagccaaga atatgtaaca gaaacagcca      480
aacaagaaaa agaaaaagcc tttatggtcg gtactgaatt atcatatgca ggtttagcac      540
taggtgttga ctacgcacaa                                                  560
```

```
<210> SEQ ID NO 10
<211> LENGTH: 539
<212> TYPE: DNA
<213> ORGANISM: Artificial Sequence
<220> FEATURE:
<223> OTHER INFORMATION: OmpH-t3

<400> SEQUENCE: 10
atccagaatt caacggtttc acatttggtg gtgcttatgt cttctcagcg ggtgctgaca      60
aacaagcagc acgtgacggt cgcggtttcg ttgtagcagg tttatacaac agaaaaatgg    120
gtgatgttgg tcttgcactt gaagcaggct atagccaaga atatgtaaca gaaacagcca    180
aacaagaaaa agaaaaagcc tttatggtcg gtactgaatt atcatatgca ggtttagcac    240
taggtgttga ctacgcacaa tctaaagtga ctaacgtaga tggtaaaaaa cgtgcacttg    300
aagtgggctt aaactatgac cttaacgata aagcgaaagt ttacactgat ttgatttggg    360
cgaaaaaagg tccaaaaggt gcgactacaa gagatcgcgc tatcatctta ggtgcgggct    420
acaaacttca caaacaagtt gaaactttg ttgaaggtgg ttggggcaga actaaaaaag    480
cagctggcgt aacaactaaa gataacaaag ttggcgttgg tttacgcgta cacttctaa     539

<210> SEQ ID NO 11
<211> LENGTH: 260
<212> TYPE: DNA
<213> ORGANISM: Artificial Sequence
<220> FEATURE:
<223> OTHER INFORMATION: OmpH-t4

<400> SEQUENCE: 11
atccagaatt caacggtttc acatttggtg gtgcttatgt cttctcagcg ggtgctgaca      60
aacaagcagc acgtgacggt cgcggtttcg ttgtagcagg tttatacaac agaaaaatgg    120
gtgatgttgg tcttgcactt gaagcaggct atagccaaga atatgtaaca gaaacagcca    180
aacaagaaaa agaaaaagcc tttatggtcg gtactgaatt atcatatgca ggtttagcac    240
taggtgttga ctacgcacaa                                                260
```